United States Patent [19]
Bres et al.

[11] 4,286,461
[45] Sep. 1, 1981

[54] METHOD AND DEVICE FOR IN SITU DETECTION OF A MINERAL DEPOSIT FLUID WITHIN A BOREHOLE

[75] Inventors: Philippe Brés, Billere; Christian Berge, Pau; Gérard Sassus-Bourda, Poey de Lescar, all of France

[73] Assignee: Societe Nationale Elf Aquitaine (Production), France

[21] Appl. No.: 90,358

[22] Filed: Nov. 1, 1979

[30] Foreign Application Priority Data

May 23, 1979 [FR] France .................... 79 13090

[51] Int. Cl.³ .................................. E21B 47/10
[52] U.S. Cl. ............................................ 73/155
[58] Field of Search ............. 73/151, 153, 579, 155; 175/40, 41, 50

[56] References Cited
U.S. PATENT DOCUMENTS

| | | | |
|---|---|---|---|
| 3,603,145 | 9/1971 | Morris | 73/155 |
| 3,648,513 | 3/1972 | Patterson | 73/53 |
| 3,776,032 | 12/1973 | Vogel | 73/155 |
| 4,130,010 | 12/1978 | Wonn | 73/19 |

FOREIGN PATENT DOCUMENTS 2271382 12/1975 France .

Primary Examiner—Jerry W. Myracle
Attorney, Agent, or Firm—Poms, Smith, Lande & Rose

[57] ABSTRACT

The amplitude variation of an acoustic wave propagated within drilling mud mixed with a mineral-deposit fluid is measured and compared with the amplitude of a reference wave obtained from the drilling mud alone. The method and the device are primarily applied to the detection of an inflow of oil or gas during a well-drilling operation.

10 Claims, 5 Drawing Figures

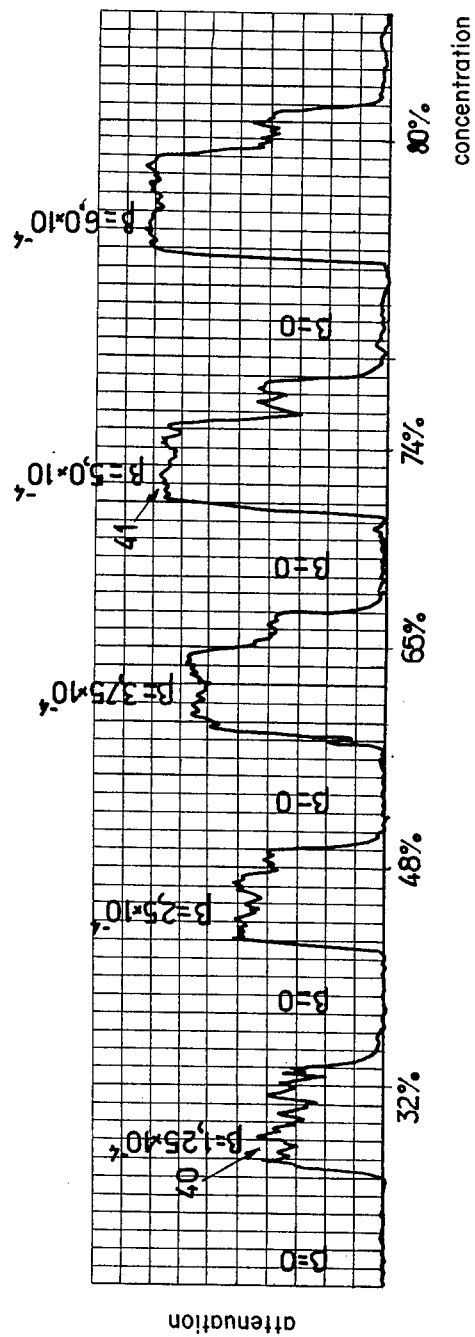

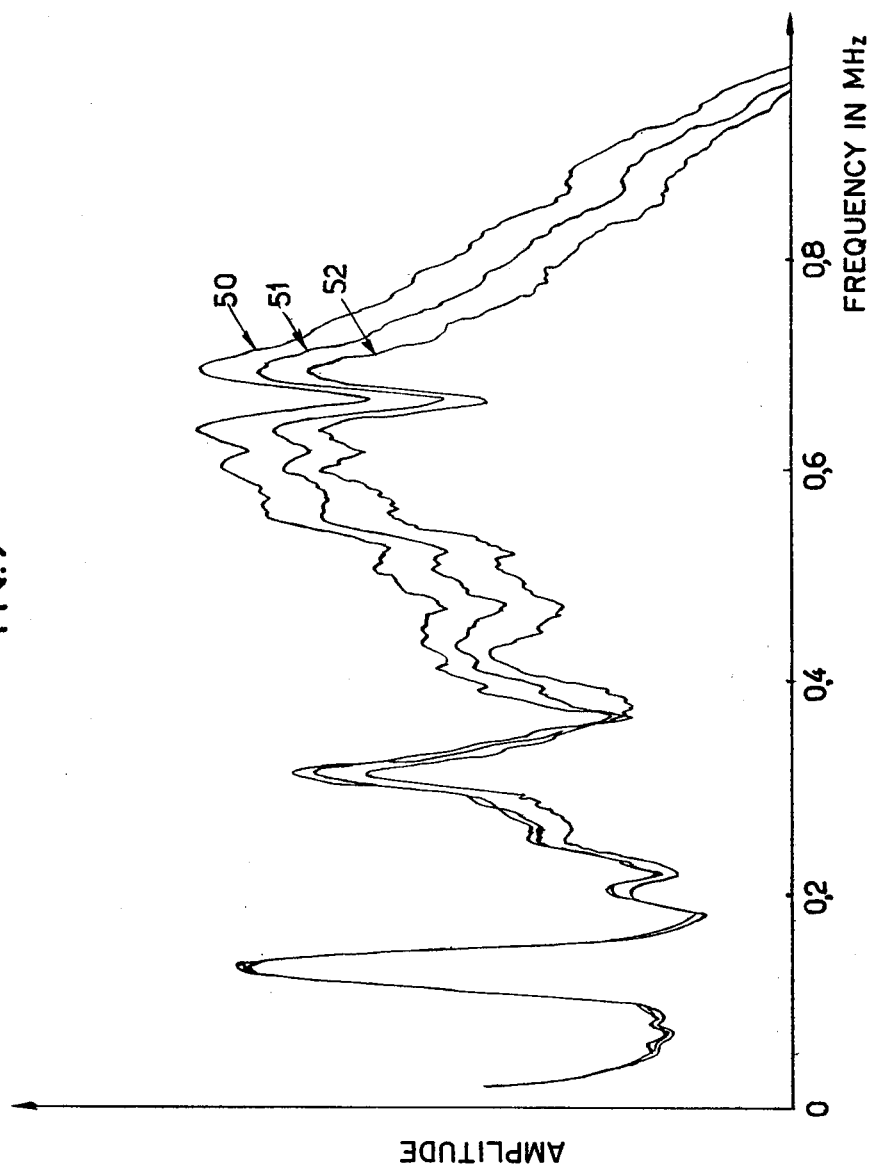

METHOD AND DEVICE FOR IN SITU DETECTION OF A MINERAL DEPOSIT FLUID WITHIN A BOREHOLE

This invention relates to a method and a device for in situ detection of a mineral deposit fluid in a drilling fluid within a borehole and more especially a gas which appears in drilling mud.

During the operation which consists in drilling a well bore in an underground formation by means of a rotary drilling bit which is driven in rotation by means of either a surface or a well-bottom drive unit, a drilling mud of known composition is circulated through the drilling bit; the mud is employed as coolant for the bit and also serves to remove cuttings as the formation is being drilled. Thus the drilling mud circulates upwards from the bottom of the borehole to the surface through the annular space formed between the drilling assembly and the wall of the borehole.

When a mineral deposit fluid originating from the drilled formation penetrates into the borehole, it mixes with the drilling mud. The problem consists in detecting the presence of said mineral deposit fluid in the drilling mud.

A number of methods and devices have been proposed. As a rule, a mineral deposit fluid is detected by waiting for the fluid to flow up to the surface with the circulated drilling mud. This method, however, does not permit accurate location of the point of introduction of the mineral deposit fluid into the borehole and/or into the drilling mud. Said method has a further disadvantage from the point of view of drilling safety and blowout prevention.

Another method consists in emitting a train of acoustic waves within the borehole both upstream and downstream of the work extremity of the drilling bit, in measuring the difference between the acoustic energy reflected and dispersed by the drilling mud upstream and downstream of said drilling bit extremity, in converting said measurement into a difference signal and in transmitting said difference signal to the surface. However, this method of well-bottom detection operates on the all-or-none principle or in other words detects only the presence or absence of a mineral deposit fluid. Moreover, the detection thresholds are too high for wells of substantial depth. Finally, it should be noted above all that this method does not permit direct measurement of the flow rate of a fluid and particularly of a gas in the drilling mud.

The aim of the present invention is to overcome the disadvantages mentioned above and to propose a method for in situ measurement and detection of a mineral deposit fluid as soon as it appears within the measurement zone. Above all, this method also plays a significant part in the achievement of enhanced operational safety in a well-drilling operation by preventing any blowouts which may otherwise occur as a result of an inrush of gas.

The present invention is directed to a method of the type which consists in emitting in the measurement zone a predetermined complex wave having a wide frequency band, in receiving the emitted wave on a receiver which is separate from the emitter and in transmitting the information received to the surface. The distinctive feature of said method lies in the fact that it consists in determining the variation in amplitude of the wave produced by the mineral deposit fluid to be detected in the drilling fluid.

One advantage of the present invention is that any appearance of even the smallest quantity of a mineral deposit fluid such as a gas is represented by a variation in the attenuation of amplitude of the acoustic wave transmitted to the receiver and that said attenuation serves to determine the concentration of gas in the drilling mud.

According to another distinctive feature of the novel method under consideration, the amplitude of the transmitted wave resulting from introduction of mineral deposit fluid into the drilling mud is compared with the amplitude of the transmitted wave in the presence of drilling mud alone and the amplitude just mentioned constitutes a reference with which all the other measured amplitudes are compared.

According to further distinctive features of the novel method, the attenuation of measured amplitudes is representative of the rate of flow of the mineral deposit fluid in the drilling fluid.

According to yet another distinctive feature, the emitted acoustic wave is a wideband noise having a frequency within the range of 0 to 2 MHz, for example. The wave can also be a sine-wave, a continuous wave or a pulsed wave having a frequency within the range of 0.6 to a few megahertz.

The devices for the practical application of the method according to the invention usually comprise a coupling interposed between the drilling bit and the lower extremity of the drill collar, a groove being formed in an external sector of the coupling and having a profile such that the flow of drilling fluid is uniform within said groove, the emitting and receiving devices being separate and housed in oppositely-facing relation within said groove.

Further advantages and distinctive features of the invention will be brought out by the preferred embodiment of the invention which is described hereinafter by way of indication but not in any limiting sense, reference being made to the accompanying drawings in which:

FIG. 4 represents the attenuation of the amplitude of signals received as a function of the volume concentration of a gas in the drilling mud;

FIG. 5 represents the signals received in respect of different volume concentrations of a gas in the drilling mud, the amplitude being plotted as ordinates and the frequency being plotted as abscissae.

Figure 2:
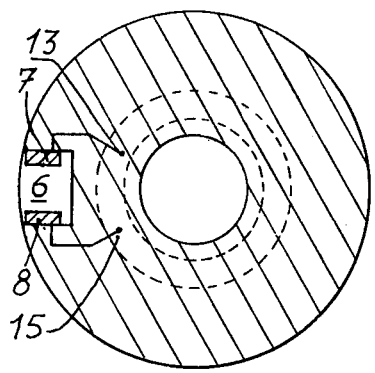
FIG. 2 is a sectional view taken along line II—II of FIG. 1.
Figure 1:
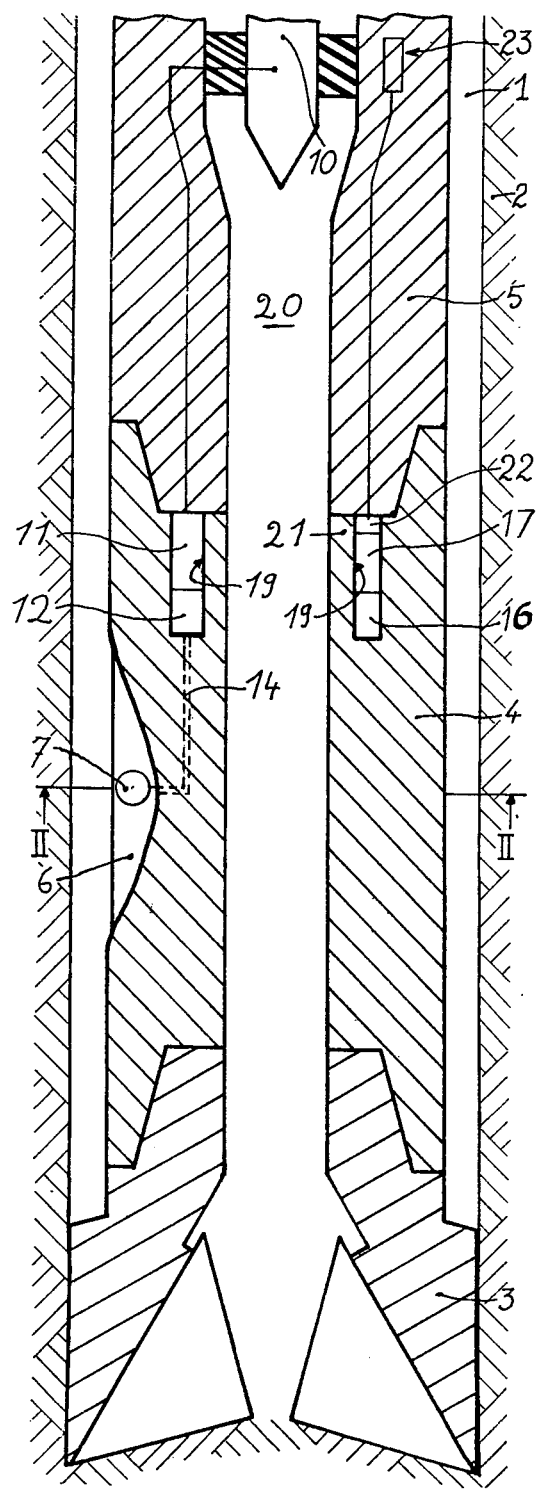
FIG. 1 is a diagrammatic vertical sectional view of a device according to the invention.
Figure 3:
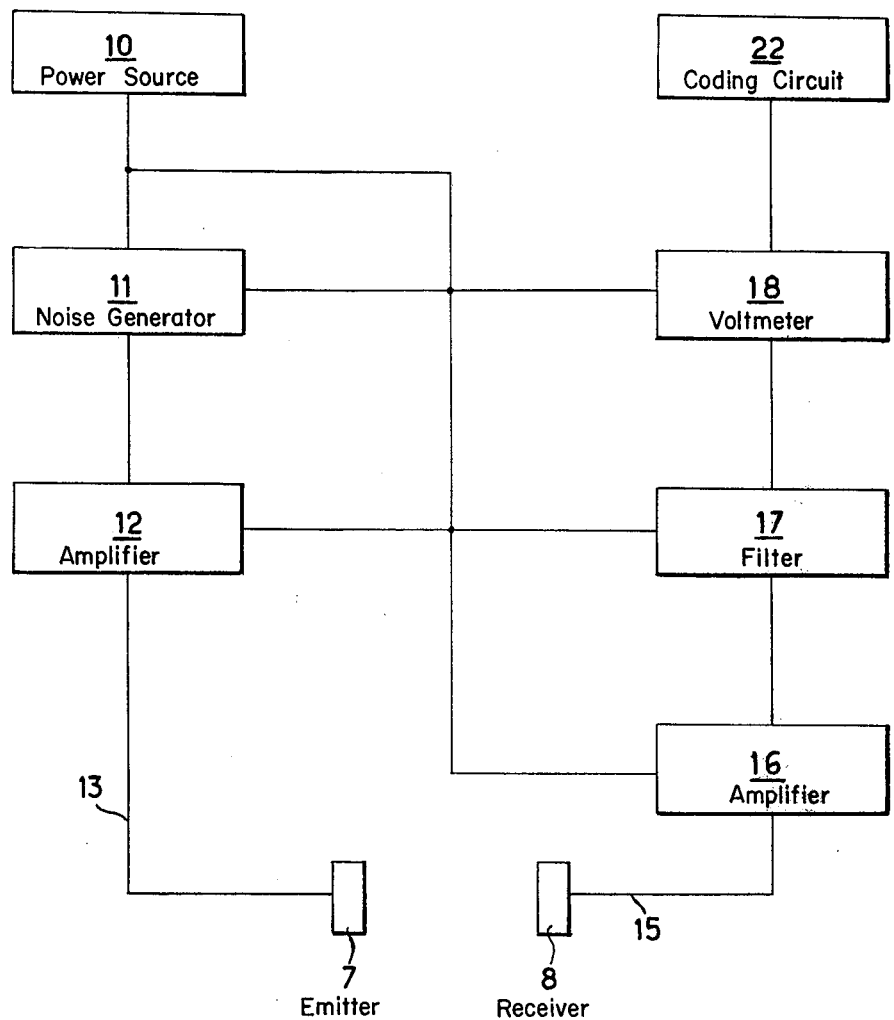
FIG. 3 is a block diagram of the device shown in FIG. 1 in the case of emission of a continuous wave.

A borehole 1 is drilled into an underground formation 2 by means of an assembly comprising a drill collar which terminates in a drilling bit 3 of a type known per se. A coupling 4 is interposed above the drilling bit 3 and connected by screwing to a transmitter 5 which is mounted at the lower end of the drill collar. The transmitter 5 is of a suitable type and operates in particular on the principle of hydraulic impulses or by means of electric cables passed through the drill pipes.

The coupling 4 is provided with a vertical groove 6 formed in a sector of the external contour of said coupling. The groove 6 has a profile which is conducive to effective flow of the drilling mud between transducers 7 and 8 housed in oppositely-facing relation within said groove. Said transducers 7 and 8 are of the ferroelectric ceramic type such as those manufactured by the company known as "Quartz et Silice", described in leaflet ref. CR 3A, and corresponding to the designation P1-60. The distance between the emitter 7 and the receiver 8 is a few centimeters and preferably three centimeters.

The transducer 7 is an acoustic wave emitter and is supplied from an electric power source 10 which forms part of the transmitter 5, is driven by a turbine which is not shown in the drawings and is actuated by the drilling mud. The electric power source 10 supplies current to a noise generator 11 connected to an amplifier 12 which is in turn connected to the acoustic wave emitter 7 by means of at least one lead-wire 13.

The connecting leads 13 are housed within a leak-tight passage 14 formed within the coupling 4. The receiver 8 is connected to an amplifier 16 by means of leads 15 housed within a leak-tight passage which is similar to the passage 14 formed within the coupling 4.

The output of said amplifier 16 is connected to a bandpass filter 17, the pass-band of which can be from 0.6 to 2 MHz, this frequency range being in fact the most sensitive to the presence of gas bubbles.

The output of said filter is connected to an r.m.s. (root-mean-square) voltmeter 18 which measures the output electrical energy of the filter.

The output signal of the voltmeter 18 is applied to the input of a coding circuit 22 which forms part of the transmitter 5. The circuit 22 codes in digital form the levels measured by the voltmeter 18. As long as the attenuation remains below 80-85%, the output levels of the filter 17 will be measured by the voltmeter 18. In the case of an attenuation exceeding 85%, a switching system (not shown but well known to anyone versed in the art) is energized and enables the voltmeter 18 to measure the output lever of a 0-0.6 MHz filter associated with the filter 17 and thus to measure high concentrations.

The generator 11, the amplifiers 12 and 16, the filter 17 and the r.m.s. voltmeter 18 are supplied with electric power from the source 10 and disposed within an annular space 19 formed in the coupling 4, said annular space being protected from the mud which circulates within the passage 20 by a wall thickness 21.

During the drilling operation, drilling mud is injected into the passage 20 and flows up towards the surface through the annular space 1. The method in accordance with the invention consists in emitting complex acoustic waves by means of the emitter 7. The acoustic waves are emitted at all frequencies within the range of 0 to 2 MHz and pass through the medium which fills the groove 6 before being received by the receiver 8.

Under these conditions and as long as the groove 6 is filled only with drilling mud, the receiver 8 picks-up a wave having an energy level $A_o$, for example. This level $A_o$ remains constant as long as a mineral deposit fluid does not mix with the mud. When a mineral deposit fluid and especially a gas penetrates into the borehole and mixes with the drilling mud, the energy level of the acoustic wave received assumes a new value $A_1$. The measurement of the energy level $A_1$ which is different from $A_o$ is representative of the appearance of a mineral deposit fluid and especially gas in the drilling mud.

Measurement of the successive energy levels $A_1$, $A_2$, $A_3$ which are different from $A_o$ is representative of a corresponding number of different values of flow rate of the gas which penetrates into the borehole.

At the surface, a suitable apparatus displays and records the coded values of the energy levels $A_o$, $A_1$, $A_2$, $A_3$, thus making it possible in real time to follow the appearance and progressive variation of a flow of gas within the drilling mud by measurement of the attenuation $(A_o - A_i)/A_o$.

Tests performed on a simulation bench under well-bottom conditions have been carried out up to a pressure of 600 bar. The device according to the present invention has made it possible to plot the curves shown in FIG. 4 under the following conditions:

FCL mud (ferrochromium ligno-sulphonate mud)
Marsh viscosity: 50
Mud flow rate: 400 l/min
Mud density: 1.1
Borehole diameter: 152.14 mm
Pressure at well bottom: 200 bar
Filter frequency: 0.4 to 1 MHz It can be observed from the graph of FIG. 4 that the reasonable detection threshold corresponds to a concentration $\beta$ which is equal to approximately 1 per 10,000 volumes (curve 40) at the well bottom, namely 2% at the surface, thus resulting in an attenuation which is substantially equal to 30% whereas an inflow of gas of 5 per 10,000 volumes at the well bottom (curve 41), namely 10% at the surface, results in an attenuation of the order of 74%. The other curves show the attenuation values as a function of different gas concentrations $\beta$ in the drilling mud.

Should the detector be required to measure very large inflow volumes corresponding for example to values of the order of 100% at the surface, an electronic gate can be provided for measuring at lower frequencies as soon as total attenuation of the signal having frequencies above 0.4 MHz has been achieved, thus making it possible to obtain different measurement scales.

Reference will now be made to FIG. 5 in which there are shown three signals received in respect of different concentrations $\beta$ and at a temperature of 66° C.; it is accordingly observed that the curve 50 is obtained when no gas is present in the drilling mud ($\beta=0$). Above 0.4 MHz, said curve 50 is distinguished from the curves 51 and 52 corresponding respectively to the concentrations $\beta = 5 \times 10^{-4}$ and $\beta = 1 \times 10^{-3}$. On the other hand, the three curves 50 to 52 practically coincide below 0.4 MHz.

What is claimed is:

1. A device for in situ detection and measurement of a mineral deposit fluid, of the type comprising an acoustic wave emitter and an acoustic wave receiver which are mounted on a drill collar substantially in the proximity of the drilling bit, means connected to the emitter and capable of generating at least one acoustic wave, means mounted partly on the drill collar and partly at the surface, said means being connected to the receiver and capable of processing the signals received by said receiver, wherein the emitter and the receiver are placed in oppositely-facing relation at a short distance from each other and are mounted on a part of the drill collar which is constituted by an external groove, said emitter and receiver being housed within said groove.

2. A device according to claim 1, wherein the groove is formed in an external sector of the drill collar and has a profile which ensures uniform flow of the drilling fluid within said groove.

3. A device according to claim 1, wherein that portion of the drill collar on which the emitter and receiver are mounted is constituted by a coupling interposed between the drilling bit and the lower end of said drill collar.

4. A device according to claim 1, wherein the receiver is connected to a bandpass filter through an amplifier, said filter being connected at the output to a root-mean-square voltmeter.

5. A method for in situ detection and measurement of a mineral deposit fluid in a drilling fluid by means of the device according to claim 1, of the type which consists in emitting a predetermined acoustic wave in the measurement zone, in receiving the emitted wave on a receiver which is separate from the emitter, in transmitting the information received to the surface, wherein an acoustic signal having a wide frequency band is emitted and the attenuation of the amplitudes of signals received are compared with the amplitude of the reference signal produced by said acoustic signal emitted in the drilling mud alone when no mineral deposit fluid is present.

6. A method according to claim 5, wherein the frequency band of the emitted signal is within the range of 0 to 2 MHz.

7. A method according to claim 5, wherein the attenuation values of the measured amplitudes are representative of the rate of flow of the mineral deposit fluid within the drilling fluid.

8. A device for in situ detection and measurement of the mineral deposit fluid in proximity to a drilling bit comprising in combination:
- a coupling member adjacent to the drill bit and forming part of a drill string supporting the drill bit,
- said coupling member being provided with an external recess in communication with space through which upflow of drilling fluid passes in the well hole;
- an acoustic wave emitter and an acoustic wave receiver mounted in spaced relation within said external recess for flow of drilling fluid therebetween;
- means connected to said wave emitter for generating an acoustic wave signal;
- and means connected to said wave receiver for processing acoustic wave signals received by said receiver and transmitting said signals to the surface.

9. A device as stated in claim 8 wherein said external recess is provided with a longitudinally arcuate concave configuration.

10. In a device as stated in claim 8 including transmitting means adjacent said coupling means.

* * * * *